(12) United States Patent
Bichler et al.

(10) Patent No.: US 12,161,575 B2
(45) Date of Patent: Dec. 10, 2024

(54) FOOT MOVEMENT DAMPING DEVICE AND SHOE

(71) Applicant: BETTERGUARDS TECHNOLOGY GmbH, Berlin (DE)

(72) Inventors: Vinzenz Bichler, Berlin (DE); Timo Stumper, Berlin (DE); Oscar Buschinger, Berlin (DE)

(73) Assignee: BETTERGUARDS TECHNOLOGY GmbH, Berlin (DE)

(*) Notice: Subject to any disclaimer, the term of this patent is extended or adjusted under 35 U.S.C. 154(b) by 465 days.

(21) Appl. No.: 17/284,259

(22) PCT Filed: Oct. 10, 2019

(86) PCT No.: PCT/EP2019/077403
§ 371 (c)(1),
(2) Date: Apr. 9, 2021

(87) PCT Pub. No.: WO2020/074606
PCT Pub. Date: Apr. 16, 2020

(65) Prior Publication Data
US 2021/0378355 A1 Dec. 9, 2021

(30) Foreign Application Priority Data
Oct. 9, 2018 (DE) ............... 10 2018 124 932.2

(51) Int. Cl.
*A61F 5/00* (2006.01)
*A43B 7/14* (2022.01)
(Continued)

(52) U.S. Cl.
CPC .............. *A61F 5/0127* (2013.01); *A43B 7/14* (2013.01); *A43B 7/20* (2013.01); *A61F 2005/0169* (2013.01)

(58) Field of Classification Search
CPC ...... A61F 5/0104; A61F 5/0111; A61F 5/019; A61F 5/0123; A61F 5/01; A61F 5/058;
(Continued)

(56) References Cited

U.S. PATENT DOCUMENTS 1,666,290 A   4/1928  Johnston
3,295,517 A * 1/1967  Stevens ................ A61F 5/0104
                                               2/22
(Continued)

FOREIGN PATENT DOCUMENTS

DE      8700201 U1   2/1987
DE      4318588 C1   8/1994
(Continued)

OTHER PUBLICATIONS

Chinese Office Action for corresponding Chinese application CN 201980080020.5, 12 pages, dated Jan. 30, 2022.
(Continued)

*Primary Examiner* — Adam Baker
(74) *Attorney, Agent, or Firm* — Ruggiero McAllister & McMahon LLC

(57) ABSTRACT

A foot movement damper for damping a foot movement via the ankle joint, and to a correspondingly configured shoe for damping a foot movement via the ankle joint. The foot movement damper includes a support arrangement for supporting on a lower leg or from proximally on the ankle bone, a retaining arrangement for retention on a foot, and a damping element for damping a relative movement between the support arrangement and the retaining arrangement.

18 Claims, 15 Drawing Sheets

(51) Int. Cl.
  *A43B 7/20* (2006.01)
  *A61F 5/01* (2006.01)
(58) Field of Classification Search
  CPC .. A61F 5/0585; A61F 5/05858; A61F 5/3723;
       A61F 5/373; A61F 5/0127; A61F 5/013;
       A61F 5/0566; A61F 5/3715; A61F
       2005/0169; A61F 2005/0179; A61F
       5/0113; A63B 21/065; A63B 21/4025;
       A63B 21/4013; A63B 21/4015; A63B
       21/4021; A63B 21/4019
  USPC .......................................................... 602/27
  See application file for complete search history.

(56) References Cited

U.S. PATENT DOCUMENTS

| | | | |
|---|---|---|---|
| 4,753,229 A | | 6/1988 | Sutherland |
| 4,815,731 A | * | 3/1989 | Suarez ................. A63B 21/055 |
| | | | 482/126 |
| 5,277,699 A | * | 1/1994 | Williamson .......... A61F 5/0118 |
| | | | 128/882 |
| 5,382,224 A | * | 1/1995 | Spangler ............... A61F 5/0113 |
| | | | 602/23 |
| 5,472,411 A | | 12/1995 | Montag et al. |
| 6,126,625 A | | 10/2000 | Lundberg |
| 7,458,950 B1 | | 12/2008 | Ivany |
| 9,579,221 B2 | | 2/2017 | Mosler et al. |
| 9,877,540 B2 | | 1/2018 | Fleuren |
| 2003/0204971 A1 | | 11/2003 | Fauver |
| 2004/0043879 A1 | * | 3/2004 | Huang .................. A61F 5/0113 |
| | | | 482/124 |
| 2005/0198869 A1 | | 9/2005 | Bouche et al. |
| 2007/0287615 A1 | * | 12/2007 | Gilchrist .............. A63B 21/055 |
| | | | 482/124 |
| 2008/0077066 A1 | * | 3/2008 | Lewis ................... A61F 5/0113 |
| | | | 602/28 |
| 2012/0029401 A1 | | 2/2012 | Caldwell et al. |
| 2015/0173926 A1 | * | 6/2015 | Bichler ................. A61F 5/0111 |
| | | | 602/12 |
| 2016/0095735 A1 | * | 4/2016 | Wenger ................. A61F 5/0113 |
| | | | 602/28 |
| 2016/0113802 A1 | | 4/2016 | Zaccaria |
| 2016/0270943 A1 | * | 9/2016 | Forrey ................. A61F 5/0113 |
| 2018/0042752 A1 | * | 2/2018 | Omarsson ............ A61F 5/0113 |

FOREIGN PATENT DOCUMENTS

| | | |
|---|---|---|
| DE | 102008008281 | 3/2016 |
| DE | 102017109877 A1 | 11/2018 |
| EP | 0824014 A1 | 2/1998 |
| WO | 2012169895 A2 | 12/2012 |
| WO | 2020074614 A1 | 4/2020 |

OTHER PUBLICATIONS

Korean Office Action for corresponding Korean application KR10-2021-7013852, 15 pages, dated Jul. 8, 2022.
German Office Action for corresponding German application DE 10 2018 124 932.2, 6 pages, dated Sep. 2, 2019.
International Search Report for corresponding International (PCT) application No. PCT/EP2019/077403, 5 pages, dated Jan. 14, 2020.
International Search Report for International (PCT) application No. PCT/EP2019/077420, 5 pages, dated Jan. 14, 2020.

* cited by examiner

FOOT MOVEMENT DAMPING DEVICE AND SHOE

TECHNICAL FIELD

The present disclosure relates to a foot movement damper for damping a foot movement via the ankle joint, and to a correspondingly configured shoe for damping a foot movement via the ankle joint.

DESCRIPTION OF THE RELATED TECHNOLOGY

It is known to stabilize the movement of the ankle joint by means of devices for limiting foot movements, in order to counteract trauma caused by an ankle sprain, that is to say a movement of the ankle joint over at least one of its ankle joint axes in a non-physiological range. The most frequent form of sprain injury is an ankle joint distortion as a stretching or tearing following an inversion. On account of the increasing inversion angle, inversion movements over an ankle joint axis result in a change of the distance between foot and lower leg. When a defined inversion angle or a defined inversion speed or inversion acceleration is exceeded, damage to the ligaments of the ankle joint or tears can occur.

To prevent this, devices are known which permit movements within a defined range and which, starting from a defined limit angle of the movement about the ankle joint axis, completely prevent movement. For this purpose, relatively rigid orthoses are known in which movements are inhibited mainly by use of splints or splint plates.

Moreover, devices or shoes are known in which a movement of the ankle joint is permitted as far as a defined limit angle of the movement and in which, on account of the structure, a movement is completely blocked starting from this limit angle. Such a device is known, for example, from EP 2717809 B1. Such devices provide no protective effect at all before the limit angle is reached. However, it is known that the risk of injury when twisting the ankle, particularly in the case of already weakened ligaments of after an injury, also depends significantly on the inversion or supination speed and the inversion or supination acceleration occurring during twisting, and not only on the inversion or supination angle. In the range below the limit (inversion or supination) angle, such devices therefore provide no protection at all. Moreover, after the limit angle is reached, the movement is completely blocked. The abrupt stop of the twisting movement places a considerable load on the structure of the ankle joint, as a result of which there is an increased risk of injury, for example tearing at the bone or a cartilage injury. Moreover, on account of this blocking of the ankle joint, the twisting movement is transmitted to the next joint. In the case of a twisting of the ankle joint, this next joint is the knee joint. On account of the considerable lever arm, the unfavourable introduction of force and the complexity of the knee joint, this can then lead to serious injuries, for example cruciate ligament tears or meniscal injuries, which, because of the way they restrict the person affected, and on account of their complexity and their limited healing, have much more negative consequences than an injury of the ankle joint.

Devices are also known which, when fitted, always allow a minimum amount of movement but block dangerous movements. DE 10 2014 107 335 A1 discloses a device for adaptive limitation of an inversion or supination movement via the ankle joint. In order to prevent the upper part of the orthosis from moving in the direction of the foot, the ankle joint orthosis disclosed therein requires a pressure-stable bar which is located on the medial side of the ankle joint and which extends between the upper region of the orthosis and the lower region of the orthosis and which has to be fixedly connected to both regions. The bar has to be configured in such a way that the tensile forces introduced into the upper region via the pull-out device on the lateral side are returned by it to the lower region as compressive forces on the medial side without deforming or buckling. This secures a position in the distal direction. However, the bar on the medial side of the foot still limits the freedom of movement of the ankle joint. Instead of the afore-mentioned support between upper and lower part, it is moreover known to provide on the upper part a fixing means for fixing the upper part to a lower leg. With the fixing means, the upper part is in this case supported from above on the ankle bone. On account of the supporting and fixing means, these devices have a heavy weight and a relatively rigid structure and poor wearing comfort.

More recent devices or shoes are also known in which a support arrangement is provided which bears on the lower leg, by means of a circumferential band being turned back in an eyelet, tightened and then fixed. By way of a damping element for damping a relative movement, this support arrangement is connected to a retaining arrangement for retention on a foot. At least at one end, the damping element is at all times fixedly connected to the shoe or to the device. Moreover, after the device or shoe has been fitted, a pretensioning arrangement always has to be pretensioned by hand in order, in the fitted state on a foot, to provide a pretensioning of the damping element and a sufficient action of the damping element and therefore of the device or the shoe.

BRIEF DESCRIPTION OF THE DISCLOSURE

Disclosed is foot movement damper for damping a foot movement via the ankle joint, comprising a support arrangement for supporting on a lower leg or from proximally on the ankle bone, a retaining arrangement for retention on a foot, preferably on a sole region, and a damping device with at least one damping element for damping a relative movement between the support arrangement and the retaining arrangement. Moreover, the foot movement damper is characterized in that the retaining arrangement comprises an articulated mounting, wherein the damping element is held at one end on the articulated mounting, and the damping element is attached to the support arrangement via at least one attachment element, preferably movably, particularly preferably displaceably, with respect to the support arrangement, wherein the articulated mounting is configured in such a way that the damping element is attached to the retaining arrangement so as to be displaceable relative to the latter within a predefined range.

By virtue of the fact that the damping element is held in an articulated manner at one end on the retaining arrangement, and the damping element is attached to the support arrangement via at least one attachment element, preferably movably, it is made possible that the damping element can move relative to the foot during a movement of the foot relative to the lower leg via the ankle joint. In other words, the damping element can move about the articulated mounting, such that the orientation of the damping element relative to the lower leg and the front of the foot, when the foot movement damper is fitted on a foot, can change its relative position. In this way, the freedom of movement of the foot is greatly increased, since a damping element secured fixedly to the device at least at one end provides a structural stiffening of the device, which is avoided by the articulated mounting.

Moreover, by virtue of the fact that it is able to realign itself during a movement of the foot via the ankle joint, the damping element can align more closely to an optimal force transmission direction which is obtained during an inversion on account of the restoring force between support arrangement and retaining arrangement. This therefore has the effect on the one hand that the damping element can provide particularly efficient retention. On the other hand, compared to conventional devices, the damping element can have still smaller dimensions, since the damping action or damping force afforded by the damping element can be utilized optimally.

Therefore, compared to conventional devices, a foot movement damper configured in this way can provide an improved protective effect and at the same time an improved freedom of movement and enhanced wearing comfort.

It has been found that, by virtue of the abovementioned improved orientation of the damping element and the improved protective effect of the damping element, it is even possible to dispense with manual pretensioning of the damping element. Moreover, it has been found that tightening and fixing the support arrangement to the lower leg can be omitted without forfeiting the protective effect for the ankle joint. By virtue of the abovementioned advantages, it may be sufficient to hold the support arrangement in position, preferably anteriorly, merely with an elastic band.

The terms lateral, medial, posterior, anterior, proximal, distal, dorsal and plantar are to be understood as corresponding to the anatomical directional designations when the foot movement damper or the shoe is fitted correctly on a foot.

In the present case, therefore, the term "lateral side" comprises an outer side of the foot movement damper. Here, the lateral side of the foot movement damper corresponds to a lateral side of a human foot or of a lower human extremity when wearing the shoe. In the state when the foot movement damper is being worn, the "lateral side" is directed away from the centre of the body of the wearer. In other words, the term "lateral side" comprises a lateral side of the human body within the meaning of (topographic) anatomy.

Accordingly, in the present case, the term "medial side" comprises an inner side of the foot movement damper. The medial side of the foot movement damper corresponds to a medial side of a human foot or of a lower human extremity when wearing the foot movement damper. In the state when the foot movement damper is being worn, the "medial side" is oriented towards the centre of the body or located in the centre. In other words, the term "medial side" comprises a medial side of the human body within the meaning of (topographic) anatomy.

Moreover, the term "dorsal" corresponds to an upper face of the foot, the term "plantar" corresponds to an underside of the foot, the term "proximal" denotes facing or located towards the centre of the body, and the term "distal" denotes facing or located away from the centre of the body.

A "heel region" comprises a region of the foot movement damper or of a shoe in which, in the state when being worn, a heel of a foot is received. Therefore, the heel region corresponds to a posterior side of the foot movement damper within the meaning of the (topographic) anatomy of the human body. Consequently, the heel region of the shoe lies opposite an anterior side.

Here, "stretch-resistant" is to be understood as any material with which tensile forces can be transmitted. Within the meaning of the application, stretch-resistant materials can have a certain initial expansibility and, starting from a certain expansion limit value or extension limit value, preferably stiffen in such a way that the expansibility is then greatly reduced compared to the initial expansibility or extensibility. In the present case, a textile braid of filaments of a stretch-resistant material can be used as a stretch-resistant band, wherein a tensile load placed on the textile braid initially causes the filaments of the textile braid to orient themselves increasingly in the longitudinal extent of the textile braid, such that a high initial expansibility is made available at the outset by the orientation of the filaments, and, after the filaments are oriented substantially in the force flow direction, the band has a stretch-resistant structure. Alternatively, the material can also have a stretch-resistant behaviour substantially directly.

In the present case, the term "ankle joint" comprises the upper and the lower ankle joint and, accordingly, the movement axis of the upper ankle joint, which substantially permits the plantar flexion and dorsal extension of the foot, and the movement axis of the lower ankle joint, which substantially permits inversion and eversion, and also supination, adduction and plantar flexion, abduction and dorsal extension.

Here, the term "ankle bone" is moreover understood as the eminence of the joint socket, the ankle mortise of the upper ankle joint. Consequently, the term "ankle bone" in the present case comprises the lateral malleolus and the medial malleolus. By virtue of the configuration of the ankle mortise as joint socket, the ankle bone has, with respect to the proximal-distal direction, a greater cross-sectional surface area compared to the proximally adjoining portion of the lower leg. Therefore, the circumference of the ankle bone is greater compared to the proximally adjoining portion.

A "damping element" is understood as a device which, in a speed-dependent or acceleration-dependent manner, damps a relative movement between two components of the damping element. Therefore, a relative movement between the support arrangement and the retaining arrangement is damped by the damping element in a speed-dependent or acceleration-dependent manner.

The damping element is preferably provided here as an adaptively damping element. In other words, below a predefined limit speed or limit acceleration, the damping element has a preferably low first damping constant, and, starting from or above the predefined limit speed or limit acceleration, a preferably higher damping constant. It is thereby possible that, below the predefined limit speed or limit acceleration, the damping element has a lower damping effect, according to the ratio of the damping constants, than it does above the limit speed or limit acceleration. It has been found that in this way, particularly during movements with moderate speeds or accelerations, an almost unimpeded mobility of the ankle joint can be made available. If an inversion occurs with high speeds and/or accelerations at which there is a danger of injuries to the ligaments of the ankle joint, the foot movement damper damps the inversion movement via the damping element, and injury is avoided.

Here, an articulated mounting or the term "held in an articulated manner" is understood in particular as meaning that the damping element has at least one degree of freedom at a connection site to the retaining arrangement. The damping element is preferably pivotable about a pivot axis, preferably at least in a predefined angle range.

According to a further embodiment, the articulated mounting can be configured as a pivot joint and/or ball joint, which is arranged at a fixed location of the retaining arrangement. This has the effect that, in a state in which the device is fitted onto a foot, in a predefined position with respect to the foot, the force introduction from the damping element into the retaining arrangement is always transmitted into the retaining arrangement and by way of the latter into the foot. The position is preferably chosen such that the force direction of a retaining force made available by the device is aligned with an inversion movement or a supination movement.

An optional embodiment of the articulated mounting that has proven particularly advantageous is one in which the retaining arrangement has a band which is fastened to the retaining arrangement at two locations spaced apart from each other and thus forms an eyelet or loop. Here, the damping element is held on the band preferably via an eyelet or loop through which the band runs. In this way, the damping element can move at least partially along the band relative to the retaining arrangement. Moreover, in this embodiment, it is possible that the damping element can be pivoted relative to the retaining arrangement.

The term "band" is understood in particular as an elongate element which on the one hand is stretch-resistant, and therefore can transmit tensile forces, and on the other hand is pliable or flexible transversely with respect to the longitudinal extent of the band, such that it can be placed transversely to its longitudinal extent onto a corresponding structure. Moreover, a band can be easily turned back. In the present case, the term band generally comprises an elongate, flexurally slack, optionally elastic element, which can have the form of an individual fibre, a fibre strand, a wire, a cord, a cable, a textile woven fabric with limited width and fixed weave edges at both sides, or similar.

According to a further embodiment, at least one attachment element is attached to the support arrangement at two different attachment points, preferably movably, particularly preferably displaceably, wherein the damping element is held displaceably on the at least one attachment element. The damping element can thus always move along the attachment element within the two attachment points and thus, during movements of the foot via the ankle joint, can always adopt the above-described favourable or even optimal orientation.

It has been found that, when the at least one attachment element preferably extends from one attachment point to the other attachment point, and the damping element is attached to the attachment element between the two attachment points, the abovementioned effect can be achieved in a particularly pronounced manner.

The attachment element is preferably made available as an elongate, stretch-resistant element, preferably in the form of a band, a lace, a yarn, a cable, a wire and/or a knit, preferably a textile knit.

According to a further embodiment, a plurality of attachment elements are provided, preferably two attachment elements. This in particular results in a specially favourable geometry with respect to a transmission of force or forwarding of force from the damping element into the attachment elements and onwards int the support arrangement. The damping force which is generated by the damping element, and which acts substantially in the direction of the central spline, can thus be transmitted in part, depending on the orientation, to the preferably two attachment elements. Each of the attachment elements preferably extends from one attachment point to another attachment point, wherein the damping element is attached, preferably displaceably, to the respective attachment element between the two attachment points. The individual attachment elements can each have their own attachment point or they meet each other at common attachment points.

A first attachment element, relative to a central spline, preferably a central axis, of the damping element is attached preferably slidably to the damping element, at a distance from the central spline, preferably from the central axis, on a first side of the damping element, and the second attachment element, relative to the central spline, preferably the central axis, of the damping element is attached preferably slidably to the damping element, at a distance from the central spline, preferably from the central axis, on a second side of the damping element. This structure leads to further improved alignability of the damping element so that it can orient itself as closely as possible and as directly as possible in the force direction.

If the distance of the attachments from the first attachment element and second attachment element to the damping element is substantially identical relative to the central spline, preferably to the central axis, then the oppositely acting moments over the distance of the attachments with respect to the central spline are also similarly high. This therefore permits a particularly efficient orientation of the damping element in the direction of a direct force flow direction.

In order to further simplify the structure of the foot movement damper, it is possible, according to a further embodiment, that the first attachment element and the second attachment element are configured as an individual part, wherein the individual part is then deflected and guided slidably at the first attachment point or the attachment point.

It has been found that, if a pocket is provided for at least partially receiving the damping element, wherein the damping element received in the pocket is arranged in the pocket in such a way as to be movable relative to the latter, the mobility of the damping element relative at least to the retaining arrangement is made easier. In other words, the pocket can at least partially provide a space for the free movement of the damping element. Moreover, the pocket can function as a protector for at least parts of the damping element. A pocket in the shape of a triangle or trapezoid widening in the proximal direction has proven particularly advantageous.

In order to achieve the free mobility of the damping element in the pocket, the pocket can preferably have a material with a low coefficient of friction, wherein the pocket is preferably connected to the retaining arrangement.

According to a further embodiment, a sheath is provided which at least partially encloses the damping element and preferably the at least one attachment element, wherein the sheath is preferably at least partially arranged inside the pocket, movably relative to the pocket. In this way, it is possible among other things to enhance the protection of the damping element or of sensitive components of the damping element. Moreover, the sheath can preferably provide a positioning of the damping element and of the at least one attachment element relative to each other.

According to a further embodiment, the support arrangement comprises a stretch-resistant region extending posteriorly from a lateral side, from the first attachment point, at least to a medial side, and preferably anteriorly back to the lateral side, to the second attachment point. This can be particularly advantageous if the damping device is arranged on a lateral side of the foot movement damper, particularly for protection of an outer ligament, in particular the anterior tibiofibular ligament and/or the fibiocalcaneal ligament, of the ankle joint.

Alternatively or in addition, the foot movement damper according to a further embodiment can be configured in such a way that a support arrangement comprises a stretch-resistant region extending posteriorly from a medial side, from the first attachment point, at least to a lateral side, and preferably anteriorly back to the medial side, to the second attachment point. This can be particularly advantageous if the damping device is arranged on a medial side of the foot movement damper, particularly for protection of an inner ligament of the ankle joint.

An embodiment that has also proven advantageous is one in which the attachment points are positioned relative to the damping element in such a way that a retaining force, arising in the damping element as a result of a foot movement via the ankle joint, is divided into a laterally and proximally acting component and a medially and proximally acting component. It is thereby particularly possible that the damping force generated by the damping element can be introduced into the support arrangement on both sides of the foot or lower leg of a person wearing the foot movement damper, such that, opposite the damping element, the support arrangement bears on the lower leg or ankle bone in the form of a linear load. In other words, the supporting action is obtained by the support arrangement being pulled at both ends, and the support arrangement can thus bear on the ankle bone substantially without being displaced.

If the stretch-resistant region, according to a further embodiment, is connected at its ends by a stretch-elastic region, wherein the stretch-elastic region preferably extends between the first attachment point and the second attachment point counter to the stretch-resistant region, this can have the effect that the support region on the body of the person wearing the foot movement damper is held in position by the stretch-elastic region. Moreover, the stretch-elastic region can at least partially provide pretensioning, which in turn can have an increasing influence on the stiffness of the support arrangement.

An opening of the support arrangement can be adjusted via the loop formation. In a loose state of the loop, the support arrangement can thus be easily fitted in place. After the support arrangement has been brought over the ankle bone, to its position posterior to the latter, the support arrangement can be applied tightly to the lower extremity of the person wearing the foot movement damper and fixed by tightening the loop via the eyelet.

According to a further embodiment, the damping element has a receptacle which is filled with a damping medium, preferably a damping fluid, and in which a pull-out body is received movably relative to the latter, wherein the pull-out body is connected to a tensioning element extending in a pull-out direction from the receptacle, wherein the receptacle is preferably arranged proximally and the tensioning element extends distally from the receptacle, wherein the tensioning element is connected in an articulated manner to the retaining arrangement, wherein the attachment of the at least one attachment element to the receptacle is preferably arranged at a distal end of the receptacle. During a relative movement of the pull-out body, and of the tensioning element secured thereon, with respect to the receptacle, the movement of the tensioning element can be damped in accordance with the geometry of the inside of the receptacle and of the pull-out body and also in accordance with the nature, in particular the viscosity, of the damping medium.

If the damping element has a receptacle in the form of a tubular first damper part, and a tensioning element in the form of a second damper part that is movable relative to the first damper part along a pull-out direction extending along the longitudinal axis of the tubular first damper part, wherein the second damper part extends partially in the interior of the tubular first damper part and has the pull-out body therein, and wherein a damping medium is moreover contained in the damping element, this has proven an advantageous embodiment. During a relative movement of the second damper part with respect to the first damper part, the movement of the second damper part can be damped in accordance with the geometry of the inside of the first damper part and of the pull-out body of the second damper part and also in accordance with the nature, in particular the viscosity, of the damping medium.

In order to provide further improved positional accuracy of the support arrangement, a volume body, preferably a pad, can be arranged above the lateral malleolus, for bearing proximally on the lateral malleolus, and/or a volume body, preferably a pad, can be arranged above the medial malleolus, for bearing proximally on the medial malleolus.

According to a further embodiment, the damping element is arranged substantially distally from the ankle bone. Here, distally from the ankle bone is to be understood as meaning that, when the foot movement damper is fitted or pulled onto a foot, the damping element is located distally from the ankle bone.

The abovementioned object is moreover achieved by a shoe for damping a foot movement via the ankle joint, having the features of claim 12. Advantageous developments are set forth in the dependent claims, the description and the appended figures.

Accordingly, a shoe for damping a foot movement via the ankle joint is proposed, comprising a sole region and, attached to the sole region, a shoe upper. According to the present disclosure, the shoe has a foot movement damper according to one of the preceding embodiments.

Since the shoe has a foot movement damper according to one of the preceding embodiments, the advantages and effects described with respect to the foot movement damper can be achieved analogously.

Moreover, a person wishing to protect his ankle joint or the ligaments thereof does not have to put on a foot movement damper and additionally a shoe, and instead he can obtain the protective effect by putting on a suitably configured shoe that already comprises the foot movement damper.

Here, a "shoe" is understood as any form of shoe-like foot apparel with an upper or shaft and, connected to the latter, a solid base or sole, in particular orthopaedic shoes, sports shoes, leisure shoes and boots or sandals. The shoe upper and/or the sole can have an uninterrupted surface, or they can simply have segments that are needed for retention and force transmission in the event of inversion or supination of the foot. The shoe can likewise have as its main structure a sock or a stocking made of a woven textile fabric or knitted textile fabric, on at least partial regions of which are arranged segments of the shoe upper and/or on the sole by means of which the forces needed for retention of the foot in the event of inversion or supination can be taken up and passed on.

According to a further embodiment, the retaining arrangement is integrated in the sole region and/or the support arrangement is integrated in a shaft region of the shoe, wherein the damping element is movable relative to the shoe upper. By virtue of the integration of support arrangement and/or retaining arrangement in the shoe, it is possible to achieve a particularly compact structure of the shoe. By providing the mobility of the damping element relative to the shoe upper, it is possible in particular that the damping element can move relative to the shoe upper during a movement of the foot about the ankle joint, which corresponds to a change of the relative position of the foot to the lower leg and likewise to the ankle bone, in order thereby to adopt the above-described orientation located near a direct force flow direction which, in the event of inversion between foot and lower leg, acts on the ligaments of the ankle joint or on the ankle joint. As has already been described above with reference to the foot movement damper, the mobility of the foot, hence the wearing comfort for the person wearing the shoe, is enhanced. Moreover, by virtue of the possibility that the damping element aligns itself close to or in the direct force direction, the protective effect that can be provided via the foot movement damper is increased by comparison with conventional shoes, without this significantly impairing the mobility via the ankle joint.

If the foot movement damper is integrated substantially completely in the shoe, the visual aspect of the shoe can be substantially maintained in relation to an embodiment without a foot movement damper. Since shoes are purchased increasingly according to their outward appearance, this has among other things the advantage that persons who consider the outward appearance of a shoe to be desirable can likewise turn to a shoe with a foot movement damper, without in so doing having to accept any subjective optical or aesthetic deficits.

Moreover, by virtue of the complete integration of the foot movement damper in the shoe, it is possible to obtain particularly good protection of the foot movement damper or of the components thereof. Furthermore, a very high positional accuracy of support element, retaining element and damping element relative to the shoe can be achieved.

In shoes in which the upper is substantially completely stretch-resistant, for example walking shoes, safety shoes or high-shaft sports shoes, for example basketball shoes, the resulting increase of the distance from the front of the foot to the region above the ankle bone has the effect that, in the event of inversion, the shaft is pulled down at or above the ankle bone in the direction of the front foot, i.e. in the distal direction. Because of this, a connection of the shaft to the body region proximally of the ankle bone is necessarily released. Therefore, according to a further embodiment, the shoe, preferably at least in a shaft region of the shoe upper below the support arrangement, has a flexible deformation portion in order to permit a relative movement of the support arrangement relative to the retaining arrangement. By means of this flexible deformation portion, it is possible that, in a movement via the ankle joint, the support arrangement and the retaining arrangement at the respective portions of the lower extremity are positioned substantially in the predefined and intended position and remain connected thereto. In other words, the contact of the support arrangement to the lower leg and upper ankle region does not tear off for example in the event of inversion, since the flexible deformation portion permits the relative movement described above.

According to a further embodiment, the pocket is connected fixedly to the shoe upper and is preferably integrated in the shoe upper. In this way, the movement space for the damping element relative to the shoe upper can be precisely predefined. Moreover, a simple integration of the foot movement damper into the shoe is permitted.

It has proven particularly advantageous if the damping element is arranged substantially distally from the ankle bone. It is in this way possible, among other things, to reduce an absolute height of the shaft of the shoe by comparison with shoes in which the damping element is arranged at the height of the ankle bone or even above the latter. For example, instead of a conventional high-cut shoe, it is thus possible to make available a mid-cut shoe offering the same or an even better protective effect, wherein, in addition to the aesthetically pleasing shape of the last-mentioned shoe, the wearing comfort can also be enhanced.

According to a further embodiment, a window, preferably a viewing window, is provided which is configured in such a way that a view of at least a part of the damping element is obtained from outside the shoe. The window can be used, for example, to allow a person to visually check the damping element, or it can even facilitate replacement or maintenance at least of parts of the damping element. The window can at least partially have a transparent material and/or can have a region in which no material at all is provided.

The damping element is preferably configured here in such a way that the operating principle of the damping element is clearly evident. Preferably, the receptacle of the damping element has a transparent region providing a view into the interior of the receptacle.

The window can preferably comprise an outer material of the shoe, preferably of the shoe upper, a region of the pocket and/or a region of the sheath. In other words, the outer material of the shoe, the region of the pocket and/or the region of the sheath can have a window or an opening.

BRIEF DESCRIPTION OF THE FIGURES

Further embodiments of the disclosure are explained in detail in the following description of the figures, in which.

DETAILED DESCRIPTION OF ILLUSTRATIVE EMBODIMENTS

Illustrative embodiments are described below with reference to the figures. Elements that are identical or similar or that have an identical action are provided with identical reference signs in the different figures, and the description dispenses to some extent with repeated description of these elements in order to avoid redundancy.

Figure 1:
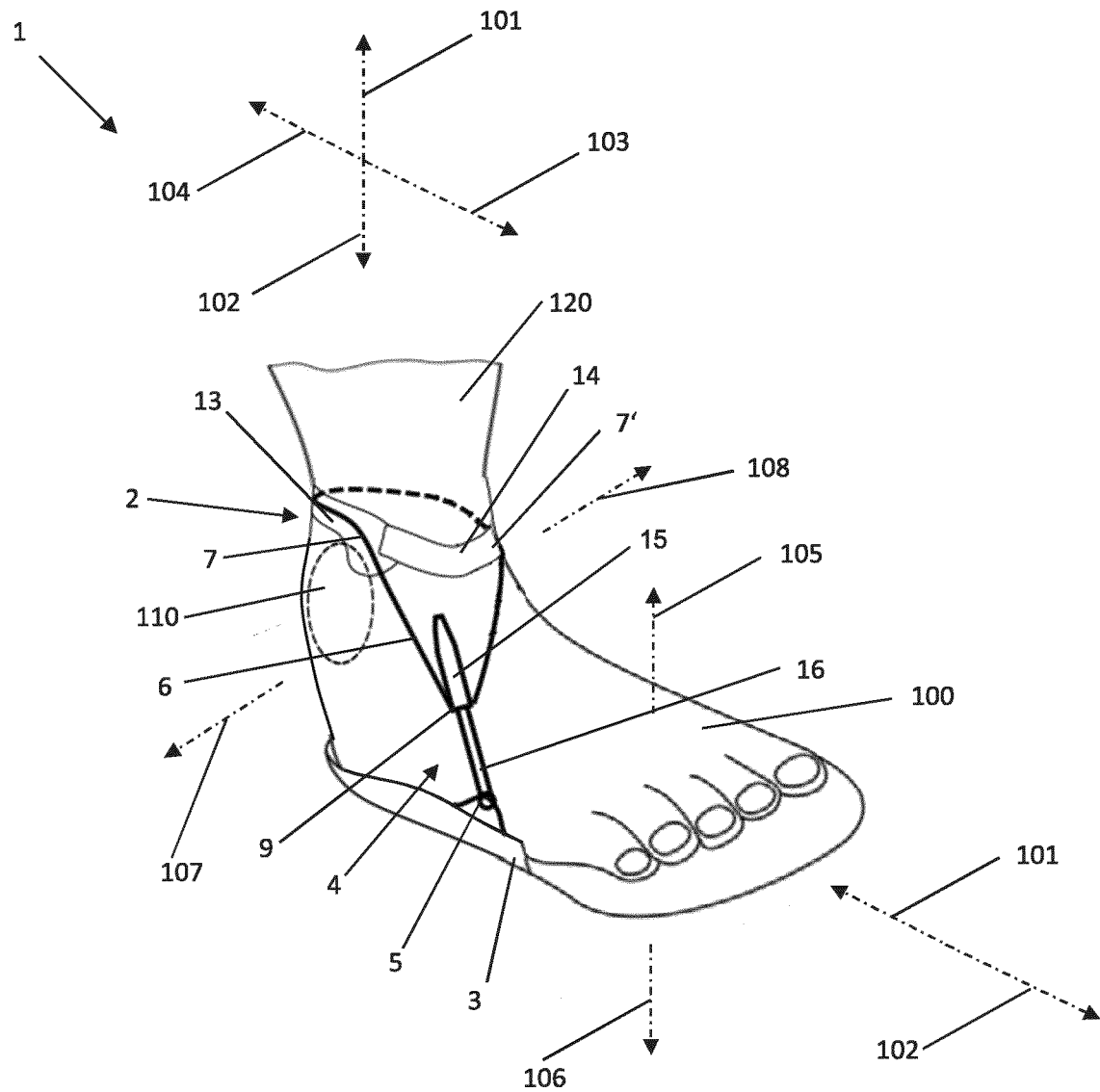
FIG. 1 shows a schematic perspective side view of a foot movement damper for damping a foot movement via the ankle joint, according to a first embodiment.

FIG. 1 shows a schematic perspective side view of a foot movement damper 1 for damping a foot movement via the ankle joint, according to a first embodiment, which is placed on a foot 100.

For better understanding, the reference signs 101-108 indicate the anatomical directions with respect to the ankle joint, and these apply analogously below in the description of the foot movement damper 1. Accordingly, the reference signs denote the following: 101 proximal, 102 distal, 103 posterior, 104 anterior, 105 dorsal, 106 plantar, 107 lateral and 108 medial.

The foot movement damper 1 has a support arrangement 2 for supporting from proximally 101 on the ankle bone 110 of the ankle joint. Moreover, it has a retaining arrangement 3 for retention on a sole region of the foot 100. Arranged between the support arrangement 2 and the retaining arrangement 3 is a damping element 4, by means of which a relative movement between the support arrangement 2 and the retaining arrangement 3 can be damped.

At its distal end, the damping element 4 is held in an articulated manner on the retaining arrangement 3 via an articulated mounting 5. Consequently, the damping element 4 is movable, about the articulated mounting 5, relative to the retaining arrangement 3 and thus also to the foot 100.

Moreover, the damping element 4 is attached to the support arrangement 2 via an attachment element 6 configured as a stretch-resistant band. The attachment element 6 extends from the support arrangement 2, from a first attachment point 7, via an attachment 9 to the damping element 4, to a second attachment point 7', at which it is again attached to the support arrangement 2. At the attachment 9, the attachment element 6 is connected displaceably to the damping element 4. In other words, the damping element 4 can move along the attachment element 6 via the attachment 9.

If a position of the foot 100 relative to the lower leg 120 changes through a movement via the ankle joint, then the damping element 4, on account of the provided free mobility relative to the retaining arrangement 3 and likewise via the displaceable attachment to the attachment element 6, is able to align itself anew relative to the support arrangement 2 according to the change of the foot position. In this way, it is possible that the longitudinal extent of the damping element 4 approximates closely to a force direction or aligns itself fully in this direction, which corresponds to a direction of a force which acts by an inversion movement on account of a damping force in the damping element 4 between support arrangement 2 and retaining arrangement 3.

The support arrangement 2 has a stretch-resistant region 13 which extends from the lateral side, starting from the first attachment point 7, posteriorly around and across a rear region of the foot 100, to the second attachment point 7' on the medial side. The attachment points 7, 7' are positioned in such a way that a retaining force arising in the damping element 4 as a result of a foot movement via the ankle joint is divided into a laterally and proximally acting component and a medially and proximally acting component.

Between the two attachment points 7, 7', a stretch-elastic region 14 extends anteriorly 103 and is configured in such a way that, when the foot movement damper 1 is fitted on the foot 100, the stretch-elastic region 14 has a predefined pretensioning, as a result of which the support arrangement 2 can be held in position relative to the ankle bone 110.

The damping element 4 has a receptacle 15 which is filled with a damping fluid and in which a pull-out body (not shown) is received movably relative to the latter, wherein the pull-out body is connected to a tensioning element 16 extending in a pull-out direction from the receptacle 15. In the present case, the receptacle 15 is arranged proximally and the tensioning element 16 is arranged distally, wherein the tensioning element 16 is connected in an articulated manner to the retaining arrangement 3 via the articulated mounting.

The attachment 9 of the attachment element 6 to the receptacle 15 is arranged at a distal end of the receptacle 15. Therefore, on the one hand, the attachment element 6 is configured with a maximum possible length. Moreover, the orientation of the components of the attachment element 6, which each extend between the first attachment point 7 and the attachment 9 and between the second attachment point 7' and the attachment 9, enclose a smaller angle with the above-described force direction. A very direct force transmission is permitted by this steep orientation of the components of the attachment element 6.

The articulated mounting 5 is here formed by a band and an eyelet, which is threaded onto the band, wherein the band is secured to the retaining arrangement 3 at two locations spaced apart from each other and a loop is thus formed. The damping element 4 is held on the band and thus on the retaining arrangement 3 via the eyelet through which the band runs. In this way, the damping element 4 can move at least partially along the band relative to the retaining arrangement 3. Moreover, it is possible that the damping element 4 can be pivoted relative to the retaining arrangement 3.

Compared to the size of the device, the band is in this case so short that the articulated mounting 5 is present substantially at a fixed location of the retaining arrangement 3. This ensures that the introduction of force into the retaining arrangement 3 takes place at a defined position relative to the foot 100, preferably in a limit range between the metatarsus and the front of the foot, and onwards into the foot 100.

The embodiment of the foot movement damper 1 according to the disclosure, as shown in FIG. 1, can be provided, for example, to be integrated in a shoe for damping a foot movement via the ankle joint. Alternatively, the foot movement damper 1 can also be worn as a separate device in a conventional shoe. For this purpose, the retaining arrangement 3 can be placed, for example, under a removable insole of the shoe, and, when the shoe is put on, the support arrangement 2 can be brought to the intended position above the ankle bone 110.

The foot movement damper 1 is here configured in such a way that the damping element 4 extends substantially distally 102, viewed relative to the ankle bone 110. In other words, the damping element 4 is arranged substantially below the ankle bone 110.

Figure 2:
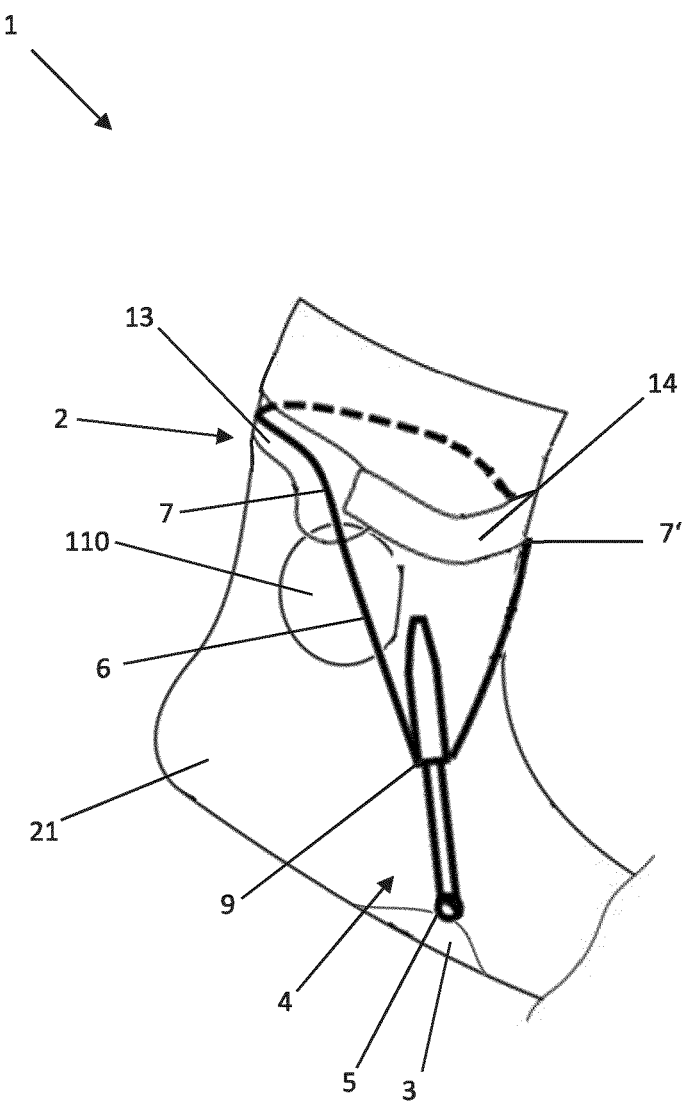
FIG. 2 shows a schematic perspective side view of a foot movement damper according to a further embodiment.

FIG. 2 shows a schematic perspective side view of a foot movement damper 1 according to a further embodiment. The foot movement damper 1 shown here substantially corresponds in its design to the one described with reference to FIG. 1, the main structure being an elastic sock 21 on which both the retaining arrangement 3 and the support arrangement 2 are mounted. The elastic sock 21 can be made available, for example, in the form of a conventional bandage. Once again, the damping element 4 is held in an articulated manner on the retaining arrangement 3 and, as has been described above, is attached several times via the attachment element 6 to the support arrangement 2. An advantage of this embodiment is that the foot movement damper 1 can be fitted by simply pulling the sock 21 on over the foot 100. Thereafter, the foot can be provided, for example, with a conventional shoe.

Moreover, the articulated mounting 5 is configured here as a pivot joint and is arranged at a fixed location of the retaining arrangement 3. The damping element 4 is therefore attached to or held on the retaining arrangement 3 so as to be pivotable relative to the retaining arrangement about a pivot axis (not shown here).

Figure 3:
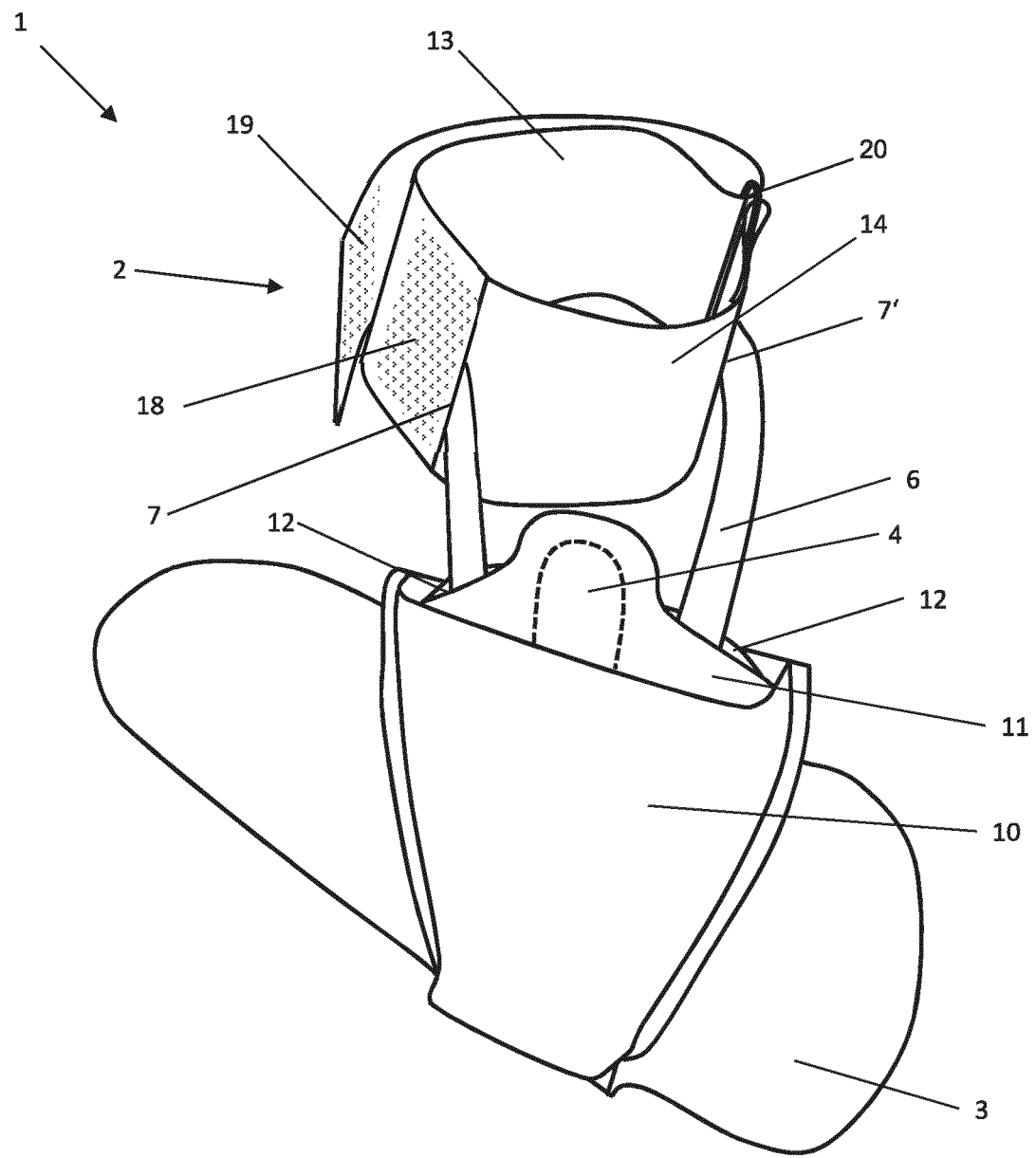
FIG. 3 shows a schematic perspective side view of a foot movement damper according to a further embodiment.

FIG. 3 shows a schematic perspective side view of a foot movement damper 1 according to a further embodiment which, for example like the device described with reference to FIG. 1, can be worn separately in a conventional shoe or else can be at least partially integrated in a shoe for damping a foot movement via the ankle joint in order to provide the aforementioned effect.

The foot movement damper 1 according to this embodiment has a sole-like retaining arrangement 3. The retaining arrangement 3 can extend substantially over the entire sole region or only over a part of the sole region of the foot.

The support arrangement 2 again has a stretch-resistant region 13 and a stretch-elastic region 14. According to this embodiment, the stretch-resistant region 13 is configured in the form of a stretch-resistant loop which is guided through an eyelet 20 and is turned back in the latter. At the end of the loop, a fastening region 19 is formed which can interact with a corresponding opposite fastening region 18 in order to permit fixing of the loop end at the region near the body. The fastening regions 18, 19 can be configured for example as a hook-and-loop fastener. The anteriorly extending stretch-elastic region 14 is sewn at one end onto the stretch-resistant region 13 and is connected to the latter at the other end via the eyelet 20.

Between the support arrangement 2 and the retaining arrangement 3, a damping element 4 is once again provided which, as described in FIGS. 1 and 2, is held in an articulated manner on the retaining arrangement 3 via an articulated mounting 5 (not shown in this figure) and is attached variously to the support arrangement 2 via an attachment element 6.

A medially extending pocket 10 is connected to the retaining arrangement 3, in which pocket 10 the damping element 4 is substantially received. The pocket 10 in this case makes available a movement space for the damping element 4, within which the latter can move freely about the movable mounting 5.

Between the pocket 10 and the damping element 4, a sheath is moreover provided which surrounds the damping element 4. The damping element 4 and the sheath 11 basically form a unit, such that the sheath 11 is also arranged movably in the pocket 10. Both the pocket 10 and the sheath 11 are made of a material, in the present case a woven fabric, that in each case has a low coefficient of friction. In this way, a smooth movement of the damping element 4 in the pocket 10 can be made available.

Moreover, on both sides of the damping element 4, the sheath 11 has a guide opening 12, in which the respective attachment element 6 is guided.

In the present case, the rear side of the pocket 10, i.e. the inner medial side near the body, is formed in one piece with the retaining arrangement 3 from a stretch-resistant woven fabric. The front of the pocket 10, i.e. the lateral side, is realized by sewing on a further piece of woven fabric. Alternatively, the pocket 10 and the retaining arrangement 3 can also be configured in another way, for example as separate components. The retaining arrangement 3 and the pocket 10 are only optionally connected to each other; they may equally not be connected to each other.

Figure 4:
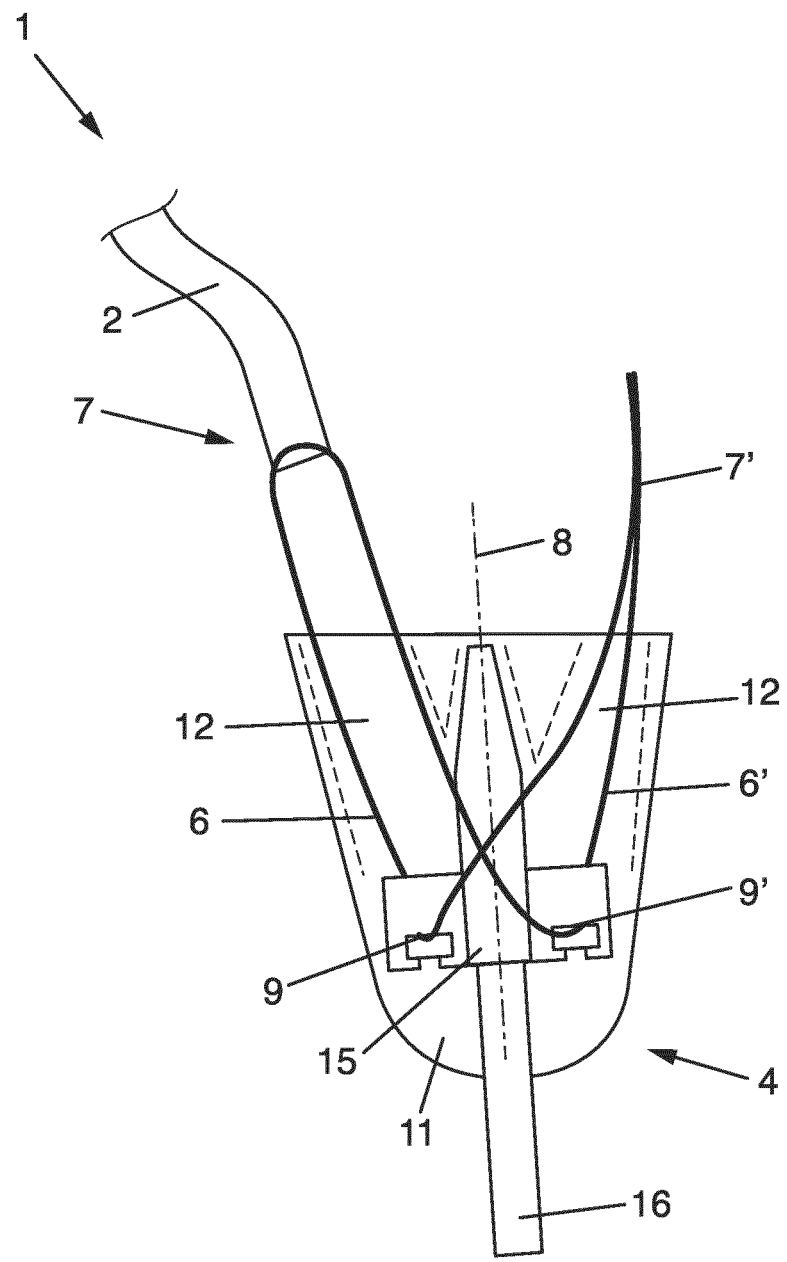
FIG. 4 shows a schematic sectional view through a sheath of a foot movement damper according to a further embodiment.

FIG. 4 shows a schematic sectional view through a sheath 11 of a foot movement damper 1 according to a further embodiment. The foot movement damper 1 corresponds substantially to the one described with reference to FIG. 3. The only difference is that here two attachment elements 6, 6' are provided for attaching to the support arrangement 2. Here, in relation to a central spline 8 of the damping element 4, which in the present case corresponds to a central axis of the receptacle 15, a first attachment element 6 is attached slidably to the receptacle 15 at a first attachment 9 on a first side, at a distance from the central spline 8, and the other attachment element 6', in relation to the central spline 8, is attached slidably to the receptacle 15 at a second attachment 9' on the opposite side, at a distance from the central spline 8.

The distance between the first attachment 9 and the central spline 8 and the distance between the second attachment 9' and the central spline 8 are optionally chosen to be the same. Alternatively, other relationships of the two distances can be provided.

The first attachment element 6 and the second attachment element 6' are in the present case formed integrally, specifically in the form of a stretch-resistant lace.

This integral individual part is secured with its two ends at the second attachment point 7'. At the first attachment point 7, the integral individual part is turned back and guided slidably on the support arrangement 2. In this way, it is possible that, during a movement of the damping element 4 relative to the support arrangement 2, the lengths resulting between the first attachment point 7 and the attachments 9, 9' and between the second attachment point and the attachments 9, 9' and the length of the first attachment element 6 relative to the length of the second attachment element 6' are modifiable. It has been found that in this way the demands on fixing the support arrangement 2 proximally from the ankle bone 110 are less than in conventional devices, and yet the same or an even better protective effect can be achieved. This also results in greater wearing comfort for the person wearing the foot movement damper 1.

Figure 5:
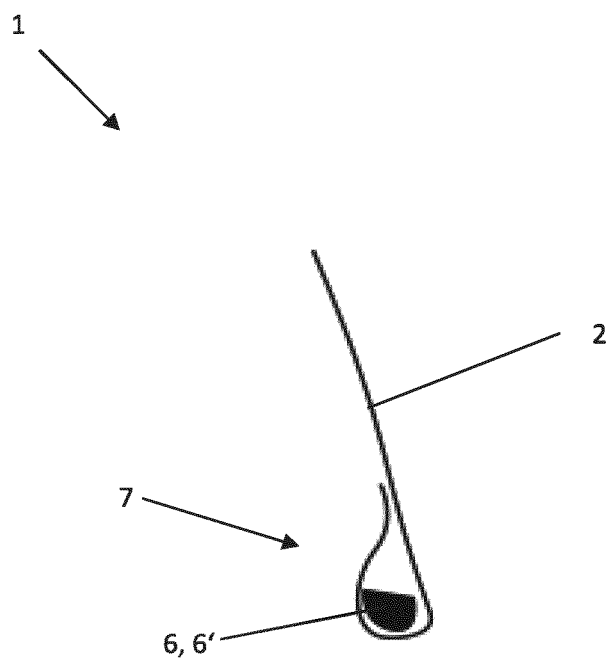
FIG. 5 shows a schematic sectional view through an attachment point of the foot movement damper according to FIG. 4.

FIG. 5 shows a schematic sectional view through the attachment point 7, in which the individual part, formed from the attachment elements 6, 6', is guided slidably.

Figure 6:
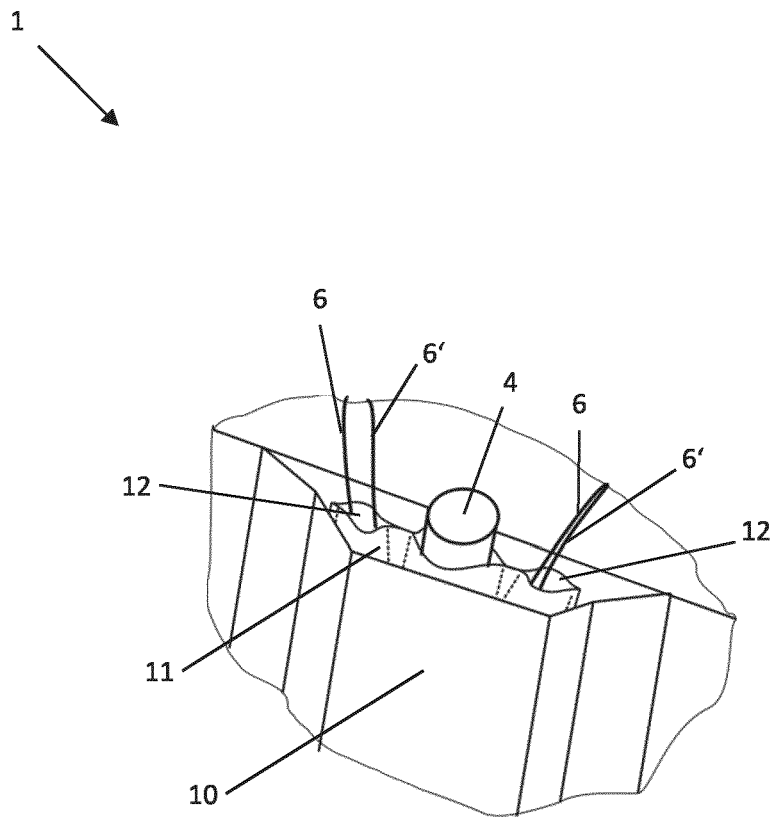
FIG. 6 shows a schematic perspective detail of the foot movement damper described with reference to FIG. 4.

FIG. 6 shows a schematic perspective detail of the foot movement damper 1 described with reference to FIG. 4. It will be clearly seen that the sheath 11 lies movably in the pocket 10. As can also be seen from FIG. 4, the guide openings 12 are configured in such a way that those components of the attachment elements 6, 6' going to the respective attachment points 7, 7' are guided in a respective guide opening 12 on one side, seen relative to the damping element 4. As a result, particularly precise guiding and positioning of the attachment elements 6, 6' are achieved by virtue of the sheath 11 with the guide openings 12.

Figure 7:
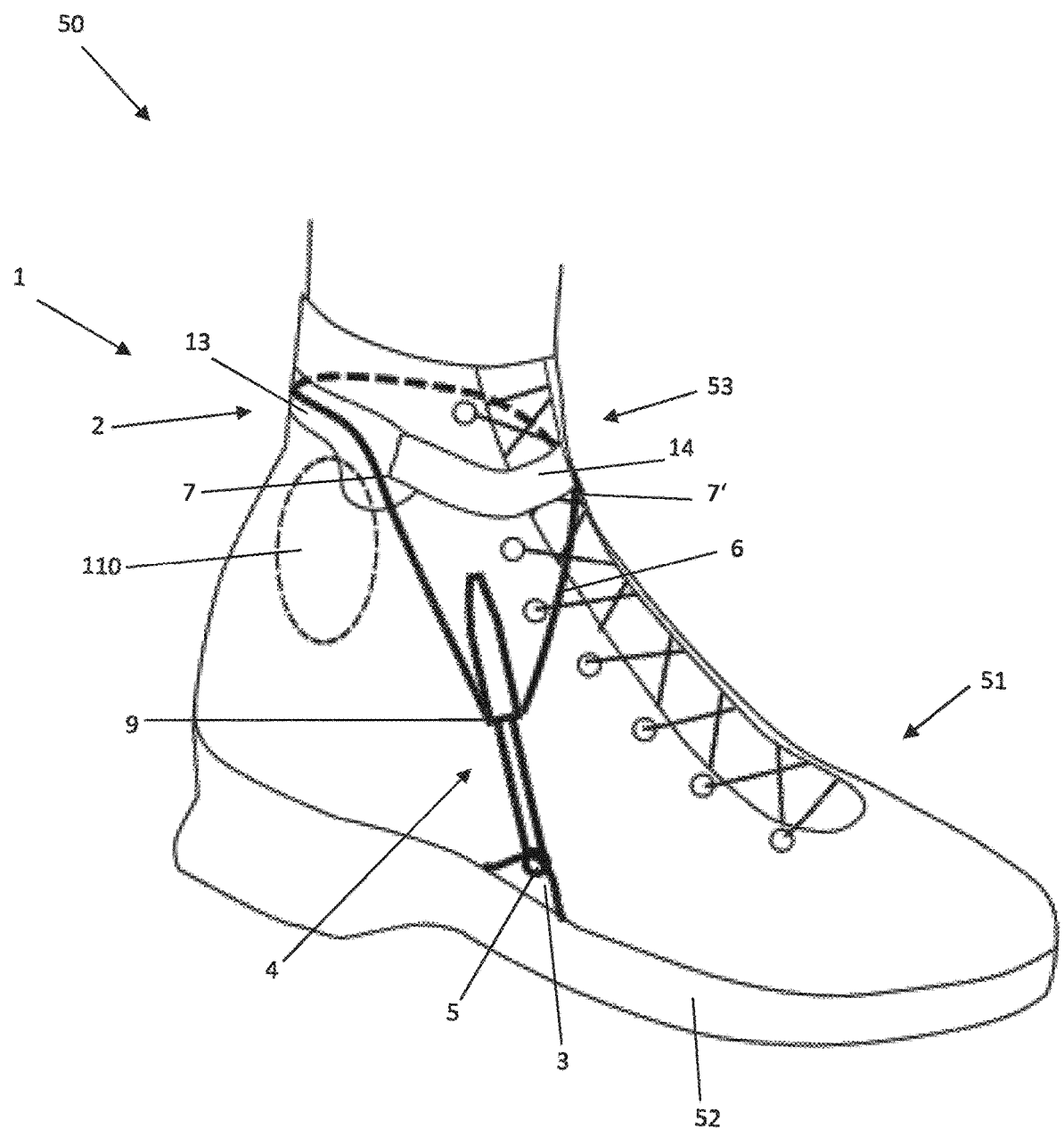
FIG. 7 shows a schematic perspective side view of a shoe according to the disclosure for damping a foot movement via the ankle joint.

FIG. 7 shows a schematic perspective side view of a shoe 50 according to the disclosure for damping a foot movement via the ankle joint. The shoe 50 has a sole region 52 and, attached to the sole region 52, a shoe upper 51. Moreover, the shoe 50 comprises a foot movement damper 1, which is configured substantially analogously to the embodiment of FIG. 1.

The retaining arrangement 3 is here integrated in the sole region 52. Therefore, the damping element 4 is movable relative to the sole region 52 via the articulated mounting 5. The support arrangement 2 is integrated in a shaft region 53 of the shoe 50. On account of the displaceable attachment of the damping element 4 to the support arrangement 2 via the attachment element 6, which again extends from the laterally arranged, first attachment point 7 to the medially arranged, second attachment point 7', the damping element 4 is arranged movably with respect to the support arrangement 2. On account of the movable attachment of the damping element 4 both to the retaining arrangement 3 and to the support arrangement 2, the damping element 4 is movable relative to the shoe upper 51.

In the shoe 50 according to this embodiment, the damping element 4 is arranged substantially distally from the ankle bone 110.

Figure 8:
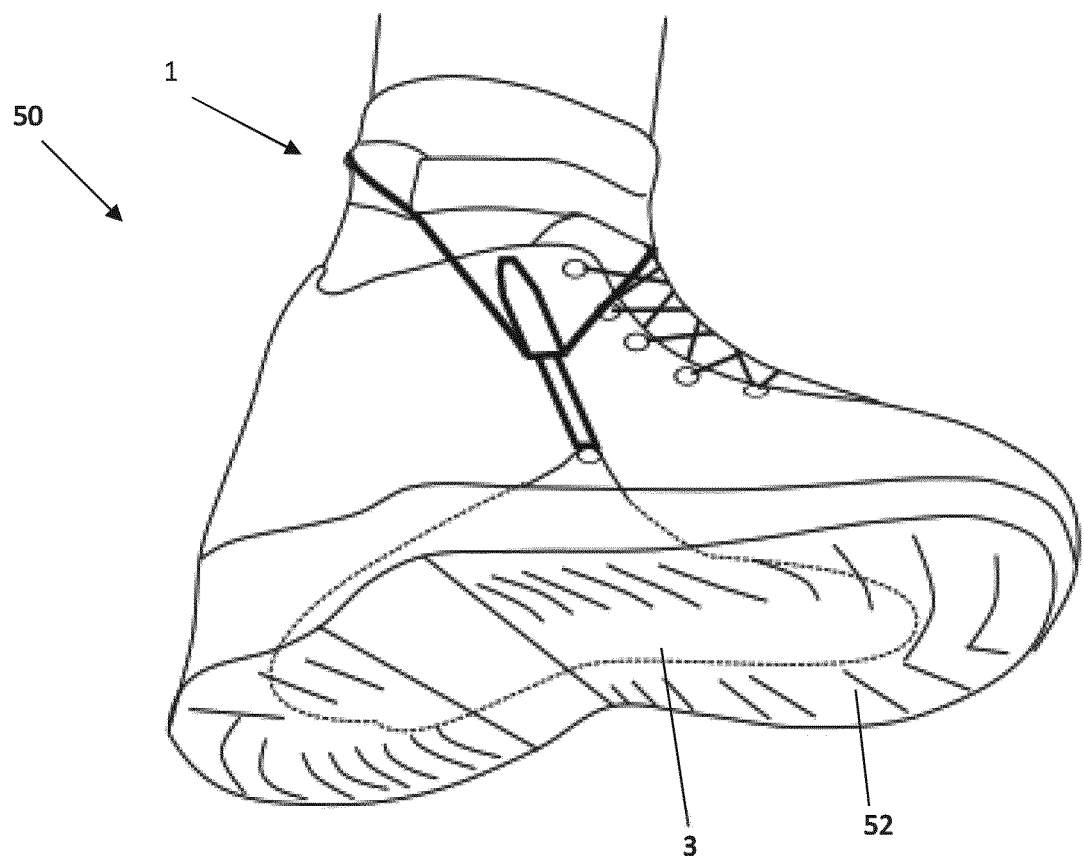
FIG. 8 shows schematically a further perspective side view of the shoe from FIG. 7.

FIG. 8 shows schematically a further perspective side view of the shoe 50 from FIG. 7. Here, the arrangement of the retaining arrangement 3 in the sole region 52 is indicated by means of a broken line.

Figure 9:
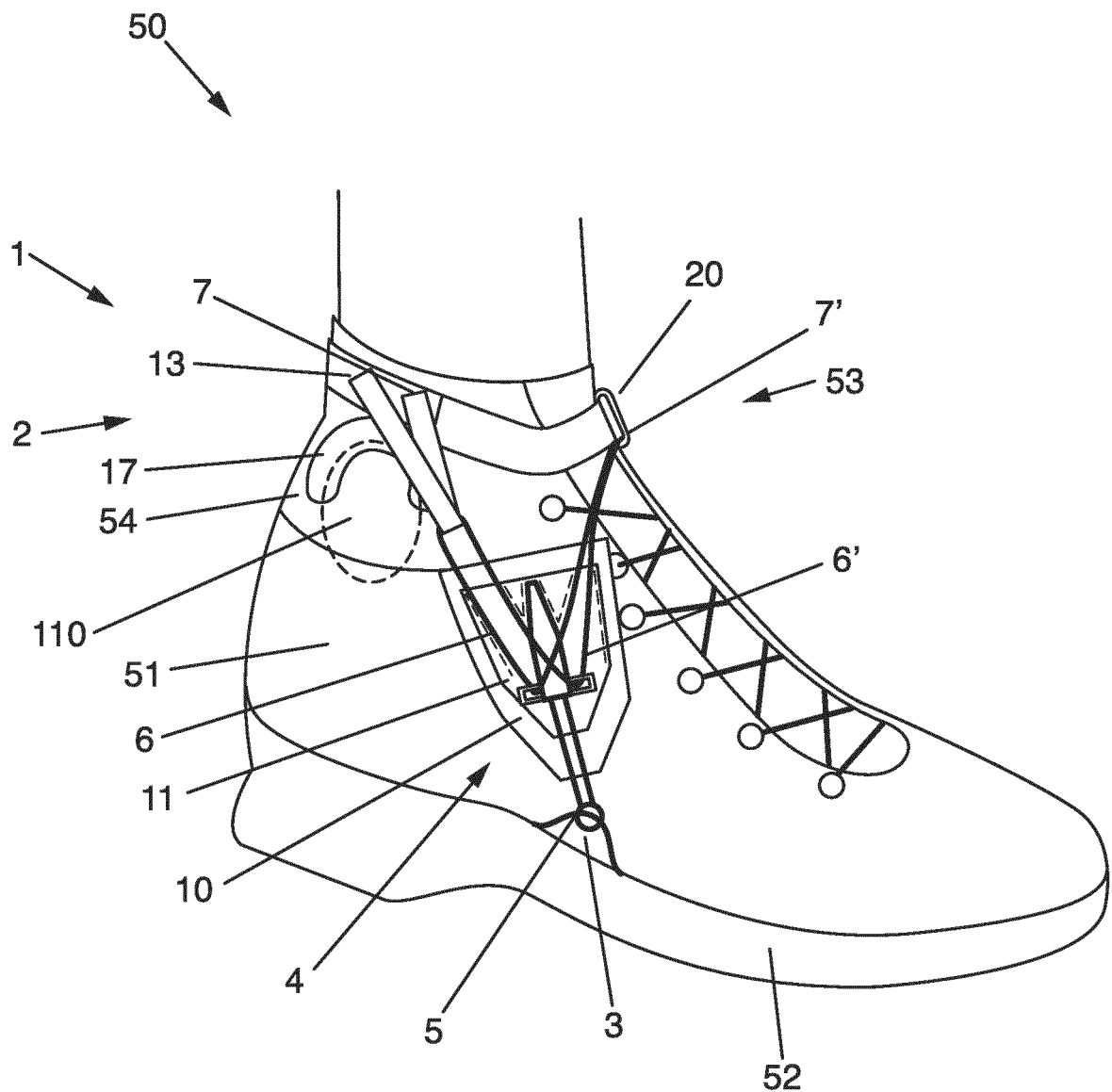
FIG. 9 shows a schematic perspective side view of a shoe according to a further embodiment.

FIG. 9 shows a schematic perspective side view of a shoe 50 according to a further embodiment. The structure of the shoe 50 corresponds substantially to that described with reference to FIG. 7. In addition, the shoe 50 according to FIG. 9 comprises a foot movement damper 1 as described with reference to FIGS. 4 to 6.

The pocket 10 is connected fixedly here to the shoe upper 51. It again makes available a movement space for the damping element 4 and the sheath 11 arranged around the damping element 4, as shown in detail in FIG. 4. The damping element 4 is arranged movably within the limits of the movement space relative to the shoe upper 51.

Moreover, the support region 2 is configured substantially as described with reference to FIG. 3. The stretch-resistant region 13 of the support arrangement 2 can thus be arranged with pretensioning on the body of the person wearing the shoe 50 by being tightened via the eyelet 20 above the ankle bone 110.

In addition, a pad 17 is provided which contributes to maintaining the support arrangement 2 at the intended position of the latter in relation to the body of the person wearing the shoe 50. In addition, the pad 17 provides better support on the ankle bone 110 from the proximal direction.

In order to make available a relative movement of the support arrangement 2 relative to the retaining arrangement 3, the above-described shoes 50 optionally have a flexible deformation portion. Various embodiments of shoes 50 with flexible deformation portions 54 are shown schematically in FIGS. 10 to 14 in which, for reasons of improved clarity, the foot movement dampers 1 integrated therein or arranged thereon are not depicted.

Figure 10:
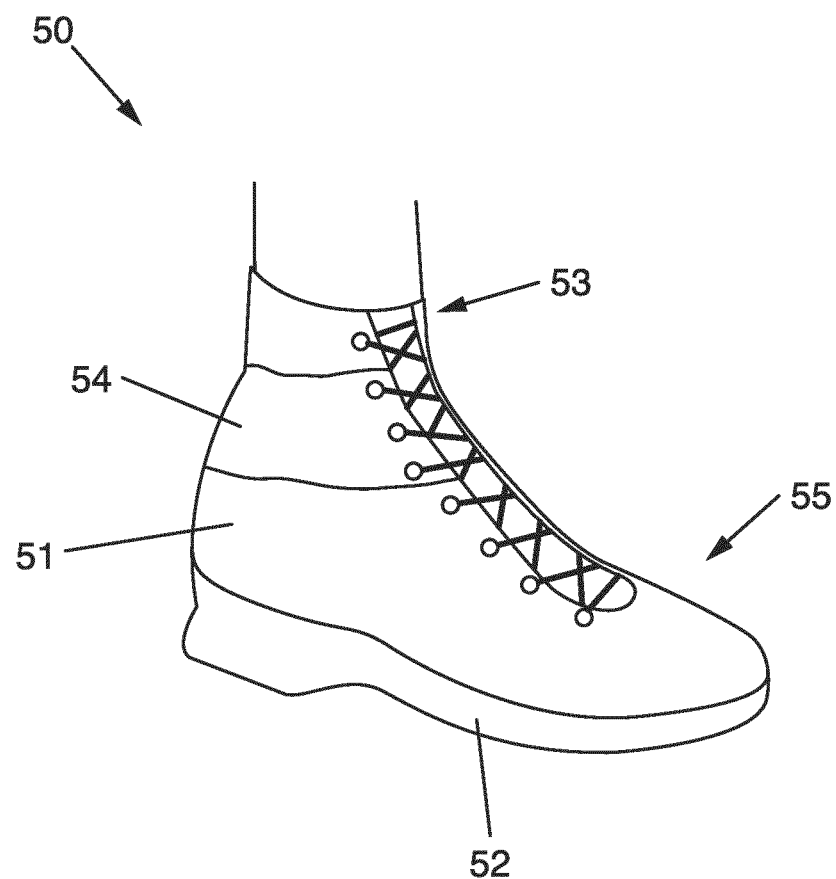
FIGS. 10 to 14 show schematically further embodiments of a shoe for damping a foot movement via the ankle joint.

In the illustrative embodiment of the shoe 50 according to FIG. 10, the flexible deformation portion 54 extends substantially fully circumferentially between the shaft 53 and a foot region 55 of the shoe upper 51. This results in a particularly high degree of mobility of the support arrangement 2, arranged on the shaft 53, relative to the retaining arrangement 3 arranged in the sole region 52. Preferably, the other regions of the shoe upper 51 are substantially stiff, preferably stretch resistant, analogously to conventional designs.

Figure 11:
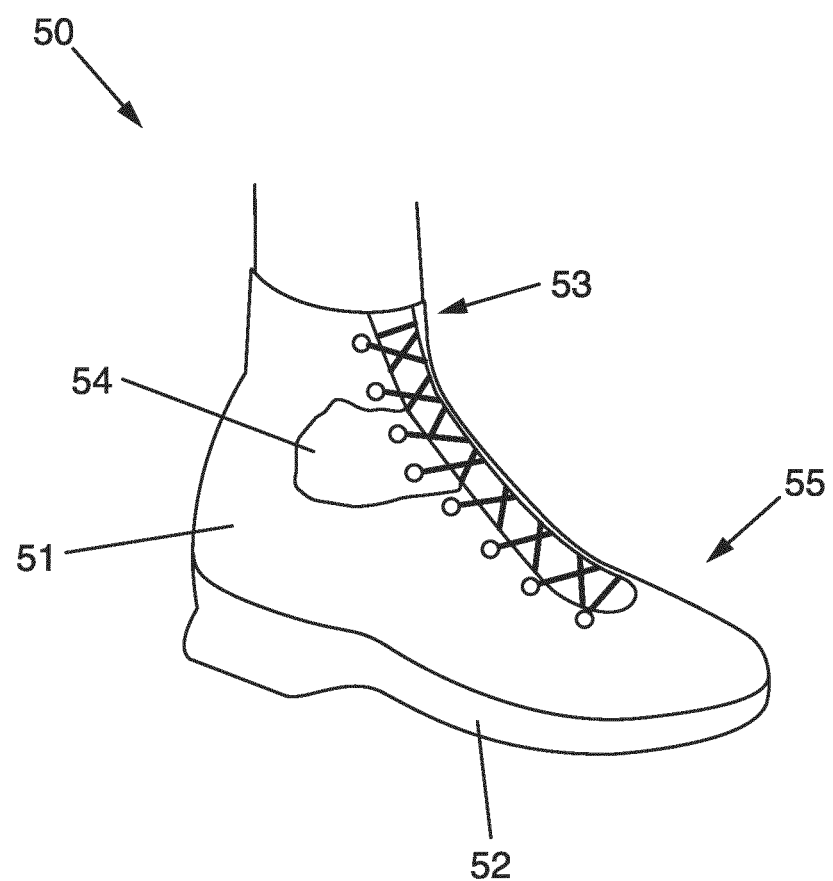

FIG. 11 shows schematically a further embodiment of a shoe 50. In contrast to what is shown in FIG. 10, the flexible deformation portion 54 extends only in a partial region, wherein the flexible deformation portion 54 is arranged in such a way that a relative movement of the support arrangement 2 relative to the retaining arrangement 3 is still permitted. This configuration has the further effect that the shaft region 53 can be additionally supported with respect to the sole region 52 via the heel region of the shoe upper 1, on account of the provision there of a relatively stiff structure of the shoe upper 51.

Figure 12:
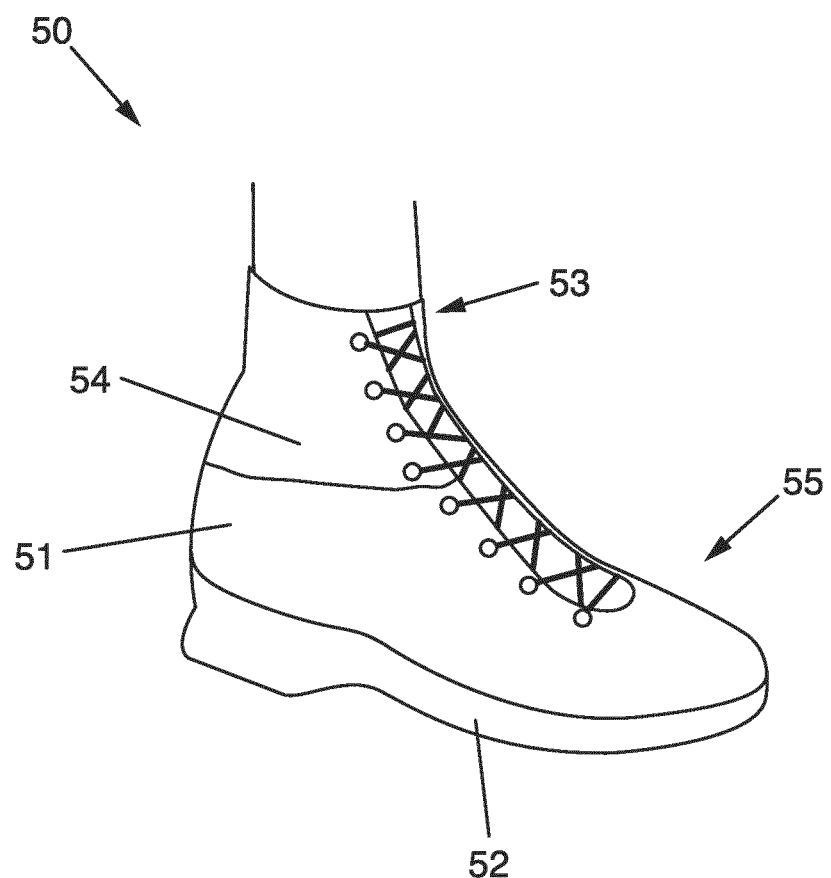

FIG. 12 shows schematically a perspective side view of a shoe 50 according to a further embodiment. Here, the entire upper portion including the complete shaft 53 is flexible. A particularly high degree of wearing comfort is thereby achieved. In shoes 50 according to this illustrative embodiment, the support arrangement 2 is configured preferably as described with reference to FIG. 3. The flexible region 54 can in the present case be realized by a sock region which is configured as part of the shoe 50 and to which the stiff region of the foot region 55 of the shoe upper 51 is connected below the ankle bone 110. Alternatively, the sock region can also extend substantially over the whole shoe 50 and/or can be configured as a sock-shaped inner shoe.

Figure 13:
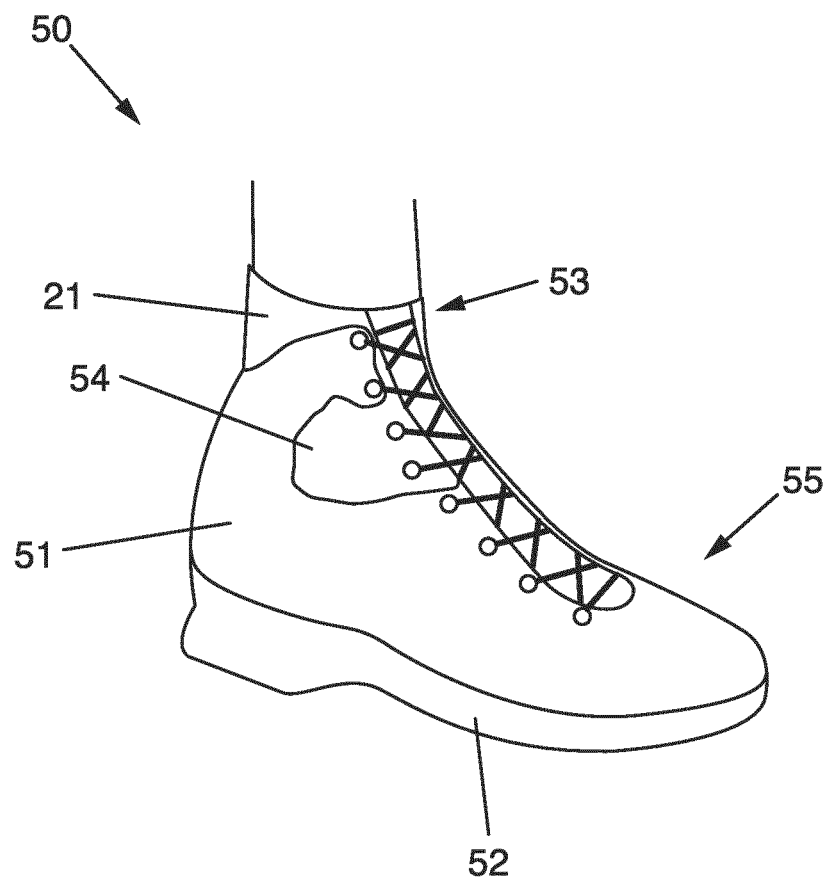

The shoe 50 shown schematically in FIG. 13 is configured substantially like the shoe in FIG. 11, wherein the sensitive deformation portion 54 additionally extends over parts of the shaft 53, as a result of which the wearing comfort is once more enhanced.

Figure 14:
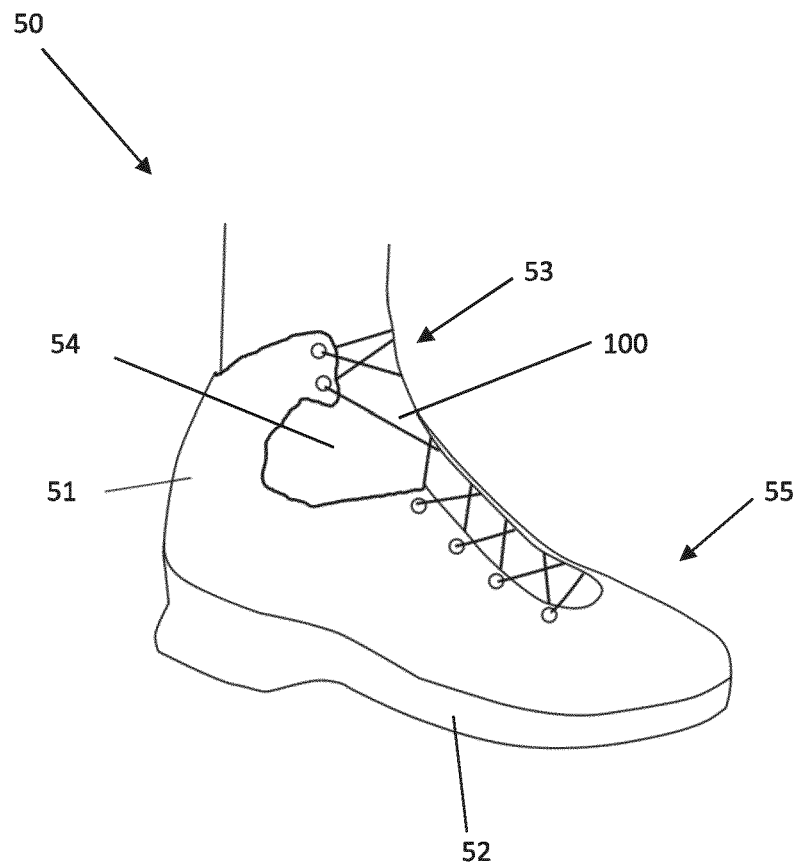

As is shown schematically in FIG. 14, a shoe 50 can optionally also have a flexible deformation portion 54 in the form of a substantially complete material cutout in this region.

Figure 15:
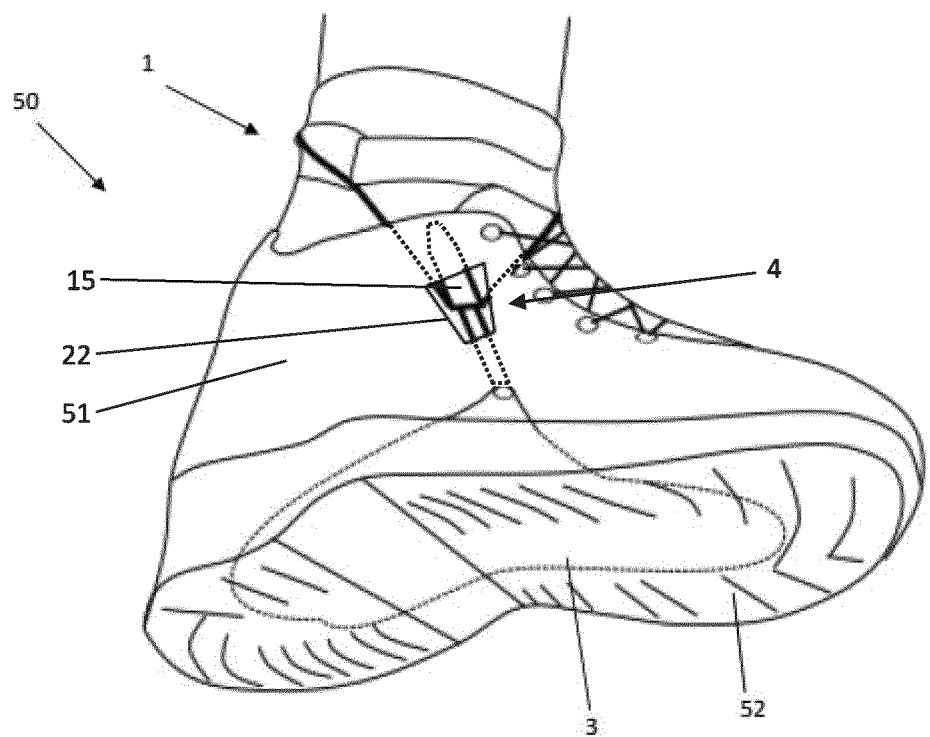
FIG. 15 shows schematically a further embodiment of a shoe for damping a foot movement via the ankle joint, in which a viewing window is provided in the shoe upper.

FIG. 15 shows schematically a further embodiment of a shoe 50 for damping a foot movement via the ankle joint. The shoe 50 is configured substantially according to the embodiment shown in FIGS. 7 and 8. However, the damping element 4 here is additionally integrated in the shoe 50. In other words, the damping element 4 is arranged inside the shoe 50, underneath an outer cover layer of the shoe upper 51, such that the damping element 4 is not visible from the outside. In addition, a viewing window 22 is provided in the shoe upper 50, through which a free view of a part of the damping element 4 is obtained from the outside. For better understanding, the covered part of the damping element 4 is indicated by broken lines.

Optionally, at least the receptacle 15 of the damping element 4 can have a transparent material at least in a partial region of the viewing window 22, such that it is then additionally possible to obtain an outside view of the pull-out body (not shown) which is movable in the receptacle 15 and which makes available the damping action.

Where applicable, all the individual features set out in the illustrative embodiments can be combined with one another and/or interchanged, without departing from the scope of the disclosure.

LIST OF REFERENCE SIGNS 1 foot movement damper
2 support arrangement
3 retaining arrangement
4 damping element
5 articulated mounting
6, 6' attachment element
7, 7' attachment point
8 central spline
9, 9' attachment
10 pocket
11 sheath
12 guide opening
13 stretch-resistant region
14 stretch-elastic region
15 receptacle
16 tensioning element
17 pad
18 fastening region
19 fastening region
20 eyelet
21 sock
22 viewing window 50 shoe
51 shoe upper
52 sole region
53 shaft region
54 flexible deformation portion
55 foot region
100 foot
101 proximal
102 distal
103 posterior
104 anterior
105 dorsal
106 plantar
107 lateral
108 medial
110 ankle bone

The invention claimed is:

1. Foot movement damper for damping a foot movement via the ankle joint, comprising a support arrangement for supporting on a lower leg or from proximally on the ankle bone, a retaining arrangement for retention on a foot, and a damping element for damping a relative movement between the support arrangement and the retaining arrangement, wherein
the retaining arrangement comprises an articulated mounting, wherein the damping element is held at one end on the articulated mounting, and the damping element is attached to the support arrangement via at least one attachment element, and wherein the articulated mounting is configured in such a way that the damping element is attached to the retaining arrangement so as to be displaceable relative to the retaining arrangement within a predefined range, and
wherein at least one attachment element is attached to the support arrangement at two different attachment points, the damping element is held displaceably on the at least one attachment element, the at least one attachment element extends from one attachment point to the other attachment point, and the damping element is attached to the attachment element between the two attachment points such that the damping element can move along the attachment element within the two attachment points and such that a longitudinal extent of the damping element substantially aligns in a force direction of a damping force in the damping element between the support arrangement and the retaining arrangement due to a change of position of the foot relative to the lower leg through a movement via the ankle joint.

2. Foot movement damper of claim 1, wherein the articulated mounting is configured as a pivot joint and/or ball joint arranged at a fixed location of the retaining arrangement, wherein the retaining arrangement has a band which is fastened to the retaining arrangement at two locations spaced apart from each other, and wherein the damping element is held on the band via an eyelet or loop through which the band runs.

3. Foot movement damper of claim 2, wherein the support arrangement comprises a stretch-resistant region extending posteriorly from a lateral side, from the first attachment point, at least to a medial side, and anteriorly back to the lateral side, to the second attachment point, and/or a support arrangement comprises a stretch-resistant region extending posteriorly from a medial side, from the first attachment point, at least to a lateral side, and anteriorly back to the medial side, to the second attachment point.

4. Foot movement damper of claim 3, wherein the attachment points are positioned relative to the damping element in such a way that a retaining force arising in the damping element as a result of a foot movement via the ankle joint is divided into a laterally and proximally acting component and a medially and proximally acting component.

5. Foot movement damper of claim 3, wherein the stretch-resistant region is connected at its ends by a stretch-elastic region, wherein the stretch-elastic region preferably extends between the first attachment point and the second attachment point counter to the stretch-resistant region.

6. Foot movement damper of claim 1, further comprising a second attachment element, wherein the first attachment element, relative to a central spline of the damping element, is attached to the damping element, at a distance from the central spline on a first side of the damping element, and
the second attachment element, relative to the central spline of the damping element, is attached to the damping element at a distance from the central spline, on a second side of the damping element,
wherein the distance of the attachments of first attachment element and second attachment element to the damping element is substantially identical relative to the central spline, and
wherein the first attachment element and the second attachment element are configured together as an individual part, and the individual part is turned back and guided slidably at the first attachment point or the second attachment point.

7. Foot movement damper of claim 6 wherein the central spline comprises a central axis and the first attachment element is relative to the central axis of the damping element is attached slidably to the damping element and at a distance from the central axis on a first side of the damping element,
the second attachment element relative the central axis of the damping element is attached slidably to the damping element at a distance from the central axis, on a second side of the damping element; and
wherein the distance of the attachments of first attachment element and second attachment element to the damping element is substantially identical relative to the central axis.

8. Foot movement damper of claim 1, wherein a pocket is provided for at least partially receiving the damping element, wherein the damping element received in the pocket is arranged in the pocket in such a way as to be movable relative to the latter, wherein the pocket preferably has a material with a low coefficient of friction, wherein the pocket is preferably connected to the retaining arrangement.

9. Foot movement damper of claim 1, wherein a sheath at least partially envelops the damping element and the at least one attachment element, wherein the sheath is preferably at least partially arranged inside the pocket movably relative to the pocket, wherein the sheath provides a positioning of the damping element and of the at least one attachment element relative to each other.

10. Foot movement damper of claim 1, wherein the damping element has a receptacle which is filled with a damping fluid and in which a pull-out body is received movably relative to the latter, wherein the pull-out body is connected to a tensioning element extending in a pull-out direction from the receptacle, wherein the receptacle is arranged proximally and the tensioning element extends distally from the receptacle, wherein the tensioning element is connected in an articulated manner to the retaining arrangement, wherein the attachment of the at least one attachment element to the receptacle is arranged at a distal end of the receptacle.

11. Foot movement damper of claim 1, wherein a volume body, preferably a pad, is arranged above the lateral malleolus, in order to bear from proximally on the lateral malleolus, and/or a volume body, preferably a pad, is arranged above the medial malleolus, in order to bear from proximally on the medial malleolus.

12. Shoe for damping a foot movement via the ankle joint, comprising a sole region and, attached to the sole region, a shoe upper, and the foot movement damper of claim 1.

13. Shoe of claim 12, wherein the retaining arrangement is integrated in the sole region and the support arrangement is integrated in a shaft region of the shoe upper, wherein the damping element is movable relative to the shoe upper.

14. Shoe of claim 12, wherein the foot movement damper is integrated substantially completely in the shoe.

15. Shoe of claim 12, further comprising a flexible deformation portion in order to permit a relative movement of the support arrangement relative to the retaining arrangement.

16. Shoe of claim 12, wherein the pocket is connected fixedly to the shoe upper and integrated in the shoe upper, and/or wherein the damping element is arranged substantially distally from the ankle bone, and/or wherein a window is provided on the shoe upper, configured in such a way that a view of at least a part of the damping element is provided from outside the shoe.

17. Shoe of claim 16, wherein the window is a viewing window.

18. The foot movement damper of claim 1, wherein the damping element is configured to be attached to the attachment element between the two attachment points on a lateral side of the foot.

\* \* \* \* \*